United States Patent
Hung et al.

(10) Patent No.: US 11,647,987 B2
(45) Date of Patent: May 16, 2023

(54) METHOD FOR GENERATING ULTRASONIC PANORAMIC IMAGE AND ULTRASONIC DEVICE USING THE SAME

(71) Applicant: QISDA CORPORATION, Taoyuan (TW)

(72) Inventors: Wei-Shin Hung, Hsinchu (TW); Fang-Bin Liu, Hsinchu (TW)

(73) Assignee: Qisda Corporation, Taoyuan (TW)

(*) Notice: Subject to any disclaimer, the term of this patent is extended or adjusted under 35 U.S.C. 154(b) by 1144 days.

(21) Appl. No.: 16/218,436

(22) Filed: Dec. 12, 2018

(65) Prior Publication Data

US 2019/0231314 A1    Aug. 1, 2019

(30) Foreign Application Priority Data

Jan. 26, 2018 (TW) ................ 107102922

(51) Int. Cl.
| | |
|---|---|
| *A61B 8/00* | (2006.01) |
| *A61B 8/08* | (2006.01) |
| *G06T 3/40* | (2006.01) |
| *H04N 5/232* | (2006.01) |

(52) U.S. Cl.
CPC ............. *A61B 8/463* (2013.01); *A61B 8/461* (2013.01); *A61B 8/488* (2013.01); *A61B 8/5246* (2013.01); *G06T 3/4038* (2013.01); *H04N 5/23238* (2013.01); *A61B 8/5253* (2013.01)

(58) Field of Classification Search
CPC .......................... A61B 8/5246; A61B 8/5253; H04N 5/23238; G06T 3/4038
See application file for complete search history.

(56) References Cited

U.S. PATENT DOCUMENTS

| | | | |
|---|---|---|---|
| 6,390,980 B1* | 5/2002 | Peterson | G01S 7/52085 600/443 |
| 6,540,681 B1* | 4/2003 | Cheng | G01S 7/52065 600/443 |
| 2002/0120195 A1* | 8/2002 | Hossack | G01S 7/52085 600/443 |
| 2005/0033173 A1* | 2/2005 | Von Behren | G01S 7/52065 600/443 |
| 2021/0219961 A1* | 7/2021 | Toyonaga | G06V 10/25 |

* cited by examiner

*Primary Examiner* — Chao Sheng (57) ABSTRACT

The invention proposes a method for generating ultrasonic panoramic image and an ultrasonic device. The invention first analyzes the degree of overlap area between two black-and-white images and determines the Doppler signal error of two corresponding color images once the overlap area is large enough. A plurality of black-and-white characteristic images and color characteristic images are then determined from the captured black-and-white images and color images and used for generating a black-and-white panoramic image and a color panoramic image respectively using an image stitching algorithm. The color panoramic image is then overlaid with the black-and-white panoramic image to form an output panoramic image.

14 Claims, 4 Drawing Sheets

METHOD FOR GENERATING ULTRASONIC PANORAMIC IMAGE AND ULTRASONIC DEVICE USING THE SAME

BACKGROUND OF THE INVENTION

1. Field of the Invention

The invention relates to an ultrasound device and method thereof and, more particularly, to an ultrasound device and method thereof capable of generating a panoramic image.

2. Description of the Prior Art

At present, a nidus with a large range can be observed and diagnosed by using ultrasound to capture images within a region of interest repeatedly and the operation depends a lot on professional knowledge and experience of an operator. Since most of ultrasound devices do not have panoramic function, it wastes time and lacks objectivity in usage. Accordingly, an ultrasound panoramic scanning capable of performing comparison for characteristic points in the images and adopting image stitching technology is unique for some applications. Specifically, the accuracy of comparison for characteristic points may be increased by edge comparison of gray-level gradient distribution or by converting information in the images into specific parameters.

The image stitching technology also affects panoramic image quality. The prior art usually performs a blur process on a seam between two images to form a seamless panoramic image. However, the resolution and details of the panoramic image may be damaged. Although the prior art has developed lots of methods for comparing characteristic points, the applicability of the prior art is limited to static tissue, such as muscle tissue, tendon tissue, ligament tissue, and so on. For example, a black-and-white ultrasound scanning is usually used to scan and generate a panoramic image with large area. As long as the scanned part is a static tissue and the subject is kept at a static state, the image will be clear. However, for dynamic tissue, such as carotid artery or blood vessels of limbs, the captured images may have sawtooth shape during the stitching process due to systolic and diastolic blood vessel, such that the panoramic image quality will be unacceptable. However, for carotid atherosclerosis screening, the ultrasound scanning is the simplest and rapidest manner for providing real information for the clinical treatment. Accordingly, how to improve the ultrasound scanning of establishing a panoramic image to improve the panoramic image quality and how to prevent the operator from making a guess and determination according to experience and knowledge are worth researching and improving.

SUMMARY OF THE INVENTION

To solve the aforesaid problems, an embodiment of the invention provides a method for generating ultrasonic panoramic image comprising steps of using an ultrasound probe to continuously obtain a plurality of black-and-white images and a plurality of color images from an object; determining a plurality of black-and-white characteristic images from the black-and-white images and determining a plurality of color characteristic images from the color images; stitching the black-and-white characteristic images to form a black-and-white panoramic image and stitching the color characteristic images to form a color panoramic image; and overlaying the color panoramic image with the black-and-white panoramic image to form an output panoramic image.

Another embodiment of the invention provides an ultrasound device comprising an ultrasound probe, a calculating unit and a display unit. The ultrasound probe continuously obtains a plurality of black-and-white images and a plurality of color images from an object. The calculating unit determines a plurality of black-and-white characteristic images from the black-and-white images and determines a plurality of color characteristic images from the color images. The calculating unit stitches the black-and-white characteristic images to form a black-and-white panoramic image and stitches the color characteristic images to form a color panoramic image. The calculating unit overlays the color panoramic image with the black-and-white panoramic image to form an output panoramic image. The display unit displays the output panoramic image.

In the embodiment of the invention, the calculating unit determines whether an overlap index between a first black-and-white image and a second black-and-white image in the black-and-white images satisfies a black-and-white predetermined value; when the overlap index between the first black-and-white image and the second black-and-white image satisfies the black-and-white predetermined value, the calculating unit determines whether an overlap index between a first color image and a second color image in the color images satisfies a color predetermined value; and when the overlap index between the first color image and the second color image satisfies the color predetermined value, the calculating unit sets the first black-and-white image, the second black-and-white image, the first color image and the second color image to be a first black-and-white characteristic image, a second black-and-white characteristic image, a first color characteristic image and a second color characteristic image.

In the embodiment of the invention, the calculating unit generates the overlap index between the first black-and-white image and the second black-and-white image according to a first characteristic algorithm.

In the embodiment of the invention, the calculating unit generates the overlap index between the first color image and the second color image according to a second characteristic algorithm.

In the embodiment of the invention, the calculating unit determines whether an overlap index between the second black-and-white image and a third black-and-white image in the black-and-white images satisfies the black-and-white predetermined value; when the overlap index between the second black-and-white image and the third black-and-white image satisfies the black-and-white predetermined value, the calculating unit determines whether an overlap index between the second color image and a third color image in the color images satisfies the color predetermined value; and when the overlap index between the second color image and the third color image satisfies the color predetermined value, the calculating unit sets the third black-and-white image and the third color image to be a third black-and-white characteristic image and a third color characteristic image.

In the embodiment of the invention, the calculating unit uses a stitching algorithm to stitch the black-and-white characteristic images to form the black-and-white panoramic image and stitch the color characteristic images to form the color panoramic image, and the stitching algorithm comprises one selected from a group consisting of Alpha mixed method, Poisson mixed method and multi-band mixed method.

In the embodiment of the invention, the ultrasound probe continuously obtains a plurality of black-and-white images and a plurality of color images from a first time point and the calculating unit generates a first output panoramic image accordingly; the ultrasound probe continuously obtains a plurality of black-and-white images and a plurality of color images from a second time point and the calculating unit generates a second output panoramic image accordingly.

In the embodiment of the invention, the ultrasound probe continuously obtains a plurality of black-and-white images and a plurality of color images from a plurality of different time points, the calculating unit generates a plurality of output panoramic images accordingly, and the display unit displays the output panoramic images to form a continuous and dynamic panoramic image.

The method and the ultrasound device of the invention at least have the following advantages.

1. No matter what kind and size of the ultrasound probe are, the invention can generate a color Doppler ultrasound panoramic image, save time without necessary to scan and observe repeatedly, and provide overall image information.

2. The invention performs screening and classification according to the information of Doppler signal to reduce error due to systolic and diastolic tissue, such that the ultrasound panoramic image is closer to real human body structure. Accordingly, the invention does not need to use additional sensor to obtain additional reference signal.

3. The invention can observe dynamic and static color Doppler panoramic image simultaneously, such that it is beneficial to observe the blood flow in the blood vessel and observe the panoramic result for a specific moment.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the following description and claims to refer to particular components. As one skilled in the art will appreciate, manufacturers may refer to a component by different names. In the following discussion and in the claims, the terms "include" and "comprise" are used in an open-ended fashion. Also, the term "couple" is intended to mean either an indirect or direct electrical/mechanical connection. Thus, if a first device is coupled to a second device, that connection may be through a direct electrical/mechanical connection, or through an indirect electrical/mechanical connection via other devices and connections. Furthermore, the term "black-and-white image" recited in the specification represents "ultrasound B mode image" and the term "color image" represents "ultrasound color mode image" well known by one skilled in the art of ultrasound image process.

Figure 1:
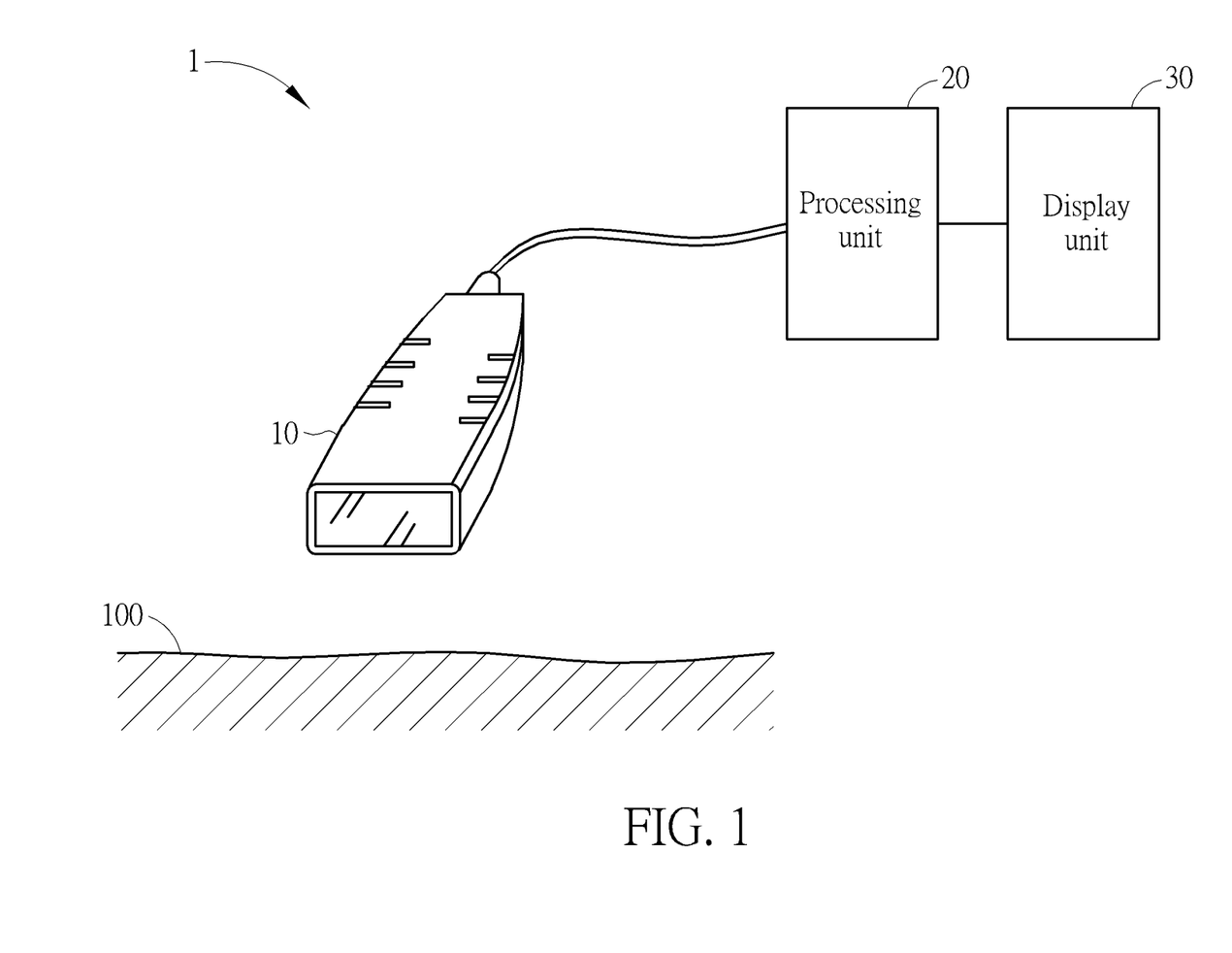
FIG. 1 is a schematic diagram illustrating an ultrasound device capable of generating a panoramic image according to an embodiment of the invention.

Referring to FIG. 1, FIG. 1 is a schematic diagram illustrating an ultrasound device capable of generating a panoramic image according to an embodiment of the invention. The ultrasound device 1 comprises an ultrasound probe 10, a calculating unit 20 and a display unit 30. The ultrasound probe 10 can continuously obtain a plurality of black-and-white images and a plurality of color images from an object 100, wherein the object 100 may be a dynamic or static tissue of a human body, such as heart, blood vessel, and so on. The calculating unit 20, which can be a processor, generates an output panoramic image according to the black-and-white images and the color images obtained by the ultrasound probe 10 and the display unit 30 displays the output panoramic image.

The ultrasound device 1 of the invention uses the ultrasound probe 10 to move on a surface of the object 100, obtains a series of black-and-white images and a series of corresponding color images in accordance with variations of time and positions, and generates a reliable panoramic image of ultrasound scanning by the two series of image information. To determine characteristic image, the invention compares characteristic points of the black-and-white ultrasound images, compares colors of the corresponding color ultrasound images in different sequences, and determines a series of black-and-white characteristic images and corresponding color characteristic images from the black-and-white images and the corresponding color images. In an embodiment, the ultrasound probe 10 obtains a plurality of color images C from the object 100 by using color Doppler ultrasound mode to perform scanning, which can measure dynamic variation of dynamic tissue including speed or intensity of blood flow and then differentiate the measured speed or intensity of blood flow by colors.

Figure 2:
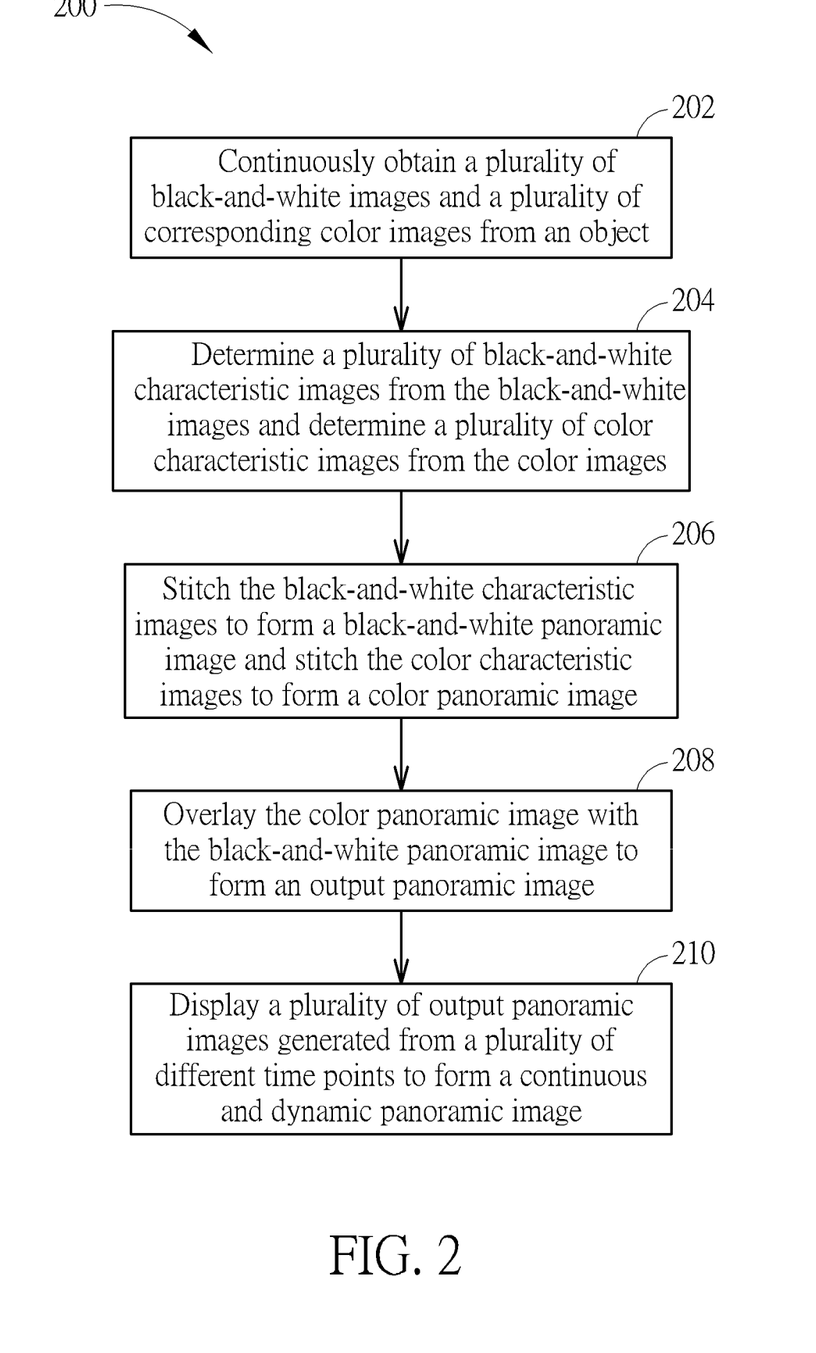
FIG. 2 is a flowchart illustrating a method using the ultrasound device shown in FIG. 1 to generate an ultrasound panoramic image.

Referring to FIG. 2, FIG. 2 is a flowchart illustrating a method 200 using the ultrasound device shown in FIG. 1 to generate an ultrasound panoramic image. The method comprises the following steps.

Step 202: continuously obtain a plurality of black-and-white images and a plurality of corresponding color images from an object.

Step 204: determine a plurality of black-and-white characteristic images from the black-and-white images and determine a plurality of color characteristic images from the color images.

Step 206: stitch the black-and-white characteristic images to form a black-and-white panoramic image and stitch the color characteristic images to form a color panoramic image.

Step 208: overlay the color panoramic image with the black-and-white panoramic image to form an output panoramic image.

Step 210: display a plurality of output panoramic images generated from a plurality of different time points to form a continuous and dynamic panoramic image.

Figure 3:
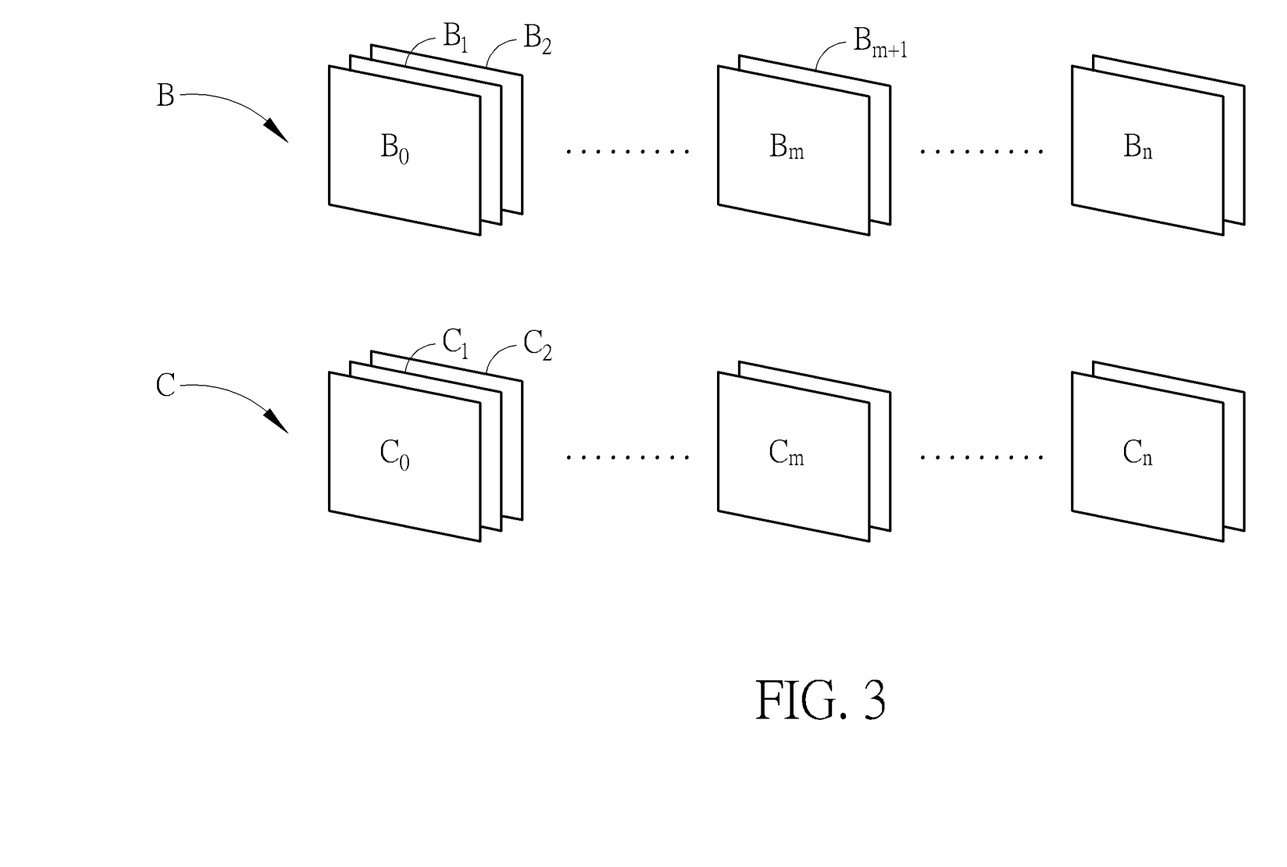
FIG. 3 is a schematic diagram illustrating a plurality of black-and-white images and a plurality of corresponding color images obtained by the ultrasound probe.

Referring to FIG. 3, FIG. 3 is a schematic diagram illustrating a plurality of black-and-white images and a plurality of corresponding color images obtained by the ultrasound probe. As recited in step 202, after using the ultrasound probe 10 to continuously obtain a plurality of black-and-white images B and a plurality of corresponding color images C from the object 100, the calculating unit 20 performs steps 204-208. In step 204, the calculating unit 20 determines a plurality of black-and-white characteristic images from the black-and-white images according to an active overlap area therebetween, wherein the determination of the black-and-white characteristic images is also determined by an active overlap area between the corresponding color images and the color image C corresponding to each black-and-white characteristic image is also recognized as a color characteristic image. Step 204 determines a plurality of black-and-white characteristic images and a plurality of color characteristic images from a series of black-and-white images B and a series of corresponding color images C and then selects the most suitable images for performing the stitching process in step 206. Then, in step 206, the calculating unit 20 stitches the black-and-white characteristic images to form a black-and-white panoramic image and stitches the color characteristic images to form a color panoramic image. During the process of stitching the characteristic images to form the panoramic image, a stitching algorithm is performed on a seam between two characteristic images to blur the seam and retain line information of the tissue. In an embodiment, the stitching algorithm may be Alpha mixed method, Poisson mixed method or multi-band mixed method. Then, in step 208, the invention overlays the color panoramic image with the black-and-white panoramic image to form an output panoramic image and then displays the output panoramic image by the display unit 30, such as a screen.

It should be noted that if step 202 is performed from different time points, the output panoramic image obtained in step 208 is different accordingly. Therefore, the invention may utilize the aforesaid characteristic to obtain different output panoramic images from different time points, wherein the output panoramic images generated from a plurality of different time points represent the tissue structures of the human body in different moments. For example, the ultrasound probe 10 continuously obtains a plurality of black-and-white images B and a plurality of corresponding color images C from a first time point (step 202) for generating a first output panoramic image (steps 204-208), continuously obtains a plurality of black-and-white images B and a plurality of corresponding color images C from a second time point (step 202) for generating a second output panoramic image (steps 204-208), and so on. Then, step 210 is performed to output the output panoramic images sequentially, so as to display a continuous and dynamic panoramic image on the display unit 30. Furthermore, the continuous and dynamic panoramic image can be paused to observe the result of the panoramic image at a specific moment.

Figure 4:
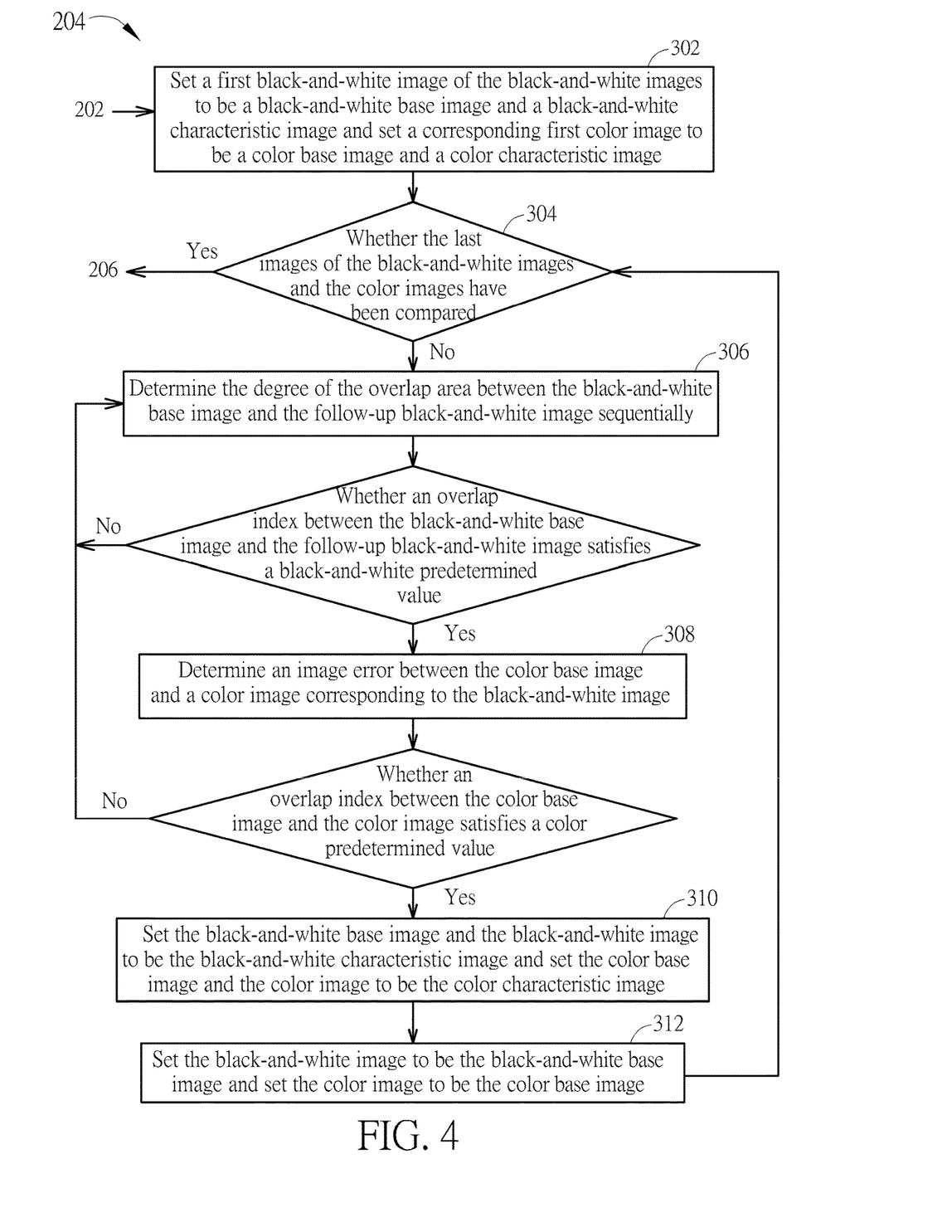
FIG. 4 is a flowchart illustrating the method using an iteration manner to determine the black-and-white characteristic images and the color characteristic images in step 204 shown in FIG. 2

The process of determining a plurality of black-and-white characteristic images and a plurality of color characteristic images in step 204 is described in the following. Referring to FIGS. 3 and 4, FIG. 4 is a flowchart illustrating the method using an iteration manner to determine the black-and-white characteristic images and the color characteristic images in step 204 shown in FIG. 2, wherein the steps are recited in the following.

Step 302: set a first black-and-white image of the black-and-white images to be a black-and-white base image and a black-and-white characteristic image and set a corresponding first color image to be a color base image and a color characteristic image.

Step 304: determine whether the last images of the black-and-white images and the color images have been compared.

Step 306: determine the degree of the overlap area between the black-and-white base image and the follow-up black-and-white image sequentially.

Step 308: determine an image error between the color base image and a color image corresponding to the black-and-white image.

Step 310: set the black-and-white base image and the black-and-white image to be the black-and-white characteristic image and set the color base image and the color image to be the color characteristic image.

Step 312: set the black-and-white image in step 310 to be the black-and-white base image, set the color image in step 310 to be the color base image, and perform step 304.

After obtaining a plurality of black-and-white images B and a plurality of corresponding color images C (as shown in FIG. 3) in step 202, two black-and-white images are inputted sequentially and a first characteristic algorithm is used to determine whether a sufficient overlap area is between the two black-and-white images. For example, in step 302, the first black-and-white image B0 of the black-and-white images B is served as a comparison base, i.e. the black-and-white image B0 is set to be a black-and-white base image and also set to be a black-and-white characteristic image. The corresponding color image C0 is set to be a color base image and also set to a color characteristic image.

The black-and-white image B0 (the first black-and-white image), which is served as the black-and-white base image, is then used to be compared with the follow-up each black-and-white image B to determine the degree of the overlap area therebetween, i.e. two input black-and-white images are compared with each other by the iteration manner (sequentially compare the black-and-white image B0 with the black-and-white image B1, compare the black-and-white image B0 with the black-and-white image B2, and so on). For example, in an embodiment, the invention may use enhanced correlation coefficient (ECC) and image registration algorithm to be the first characteristic algorithm to calculate a transition matrix to obtain the overlap area between two black-and-white images. In other embodiments, the invention may use fast feature detector (FAST), scale invariant feature transfer (SIFT), or speeded up robust features (SURF) to be the first characteristic algorithm. After performing the iteration manner again and again, an overlap index (the degree of the overlap area) between the black-and-white image B0 and the follow-up another black-and-white image Bm (second black-and-white image) satisfies a black-and-white predetermined value (step 306), i.e. a sufficient overlap area is between the black-and-white image B0 and the black-and-white image Bm, such that there is sufficient information for comparing the color images in Doppler effect.

Then, by means of an image overlap range obtained according to the black-and-white image B0 and the black-and-white image Bm, a second characteristic algorithm is used to determine an image error between the color image C0 (first color image, which is served as the color base image) with the color image Cm (second color image) corresponding to the black-and-white image Bm (step 308). In practical applications, the invention may determine whether an error (overlap index) between the color image C0 and the color image Cm is low enough, i.e. whether the overlap index also satisfies a color predetermined value. If yes, it means that a Doppler response value of the color image C0 is quite close to a Doppler response value of the color image Cm, i.e. the speed or intensity of the blood flow is quite similar. Accordingly, the black0-and-white image Bm and the corresponding color image Cm can be set to be the black-and-white characteristic image and the color characteristic image (step 310). For example, in an embodiment, the invention may use least square error method to be the second characteristic algorithm to calculate an error between two color images and determine whether the calculated error is lower than the color predetermined value. In other embodiments, the invention may use random sample consensus (RANSAC) and gradient descent to be the second characteristic algorithm.

It should be noted that if the error between the color image C0 and the color image Cm obtained by using the second characteristic algorithm in step 308 is not lower than the color predetermined value, it means that the color image Cm is unsuitable for stitching (the corresponding black-and-white image Bm will also be abandoned). Accordingly, the invention will go back to step 306 to perform the follow-up iteration and comparison. For example, the invention may compare the black-and-white image B0 with the black-and-white image Bm+1 and repeat steps 306, 308 until the aforesaid characteristic images are obtained.

After confirming that the black-and-white image Bm (second black-and-white image) and the color image Cm (second color image) are a black-and-white characteristic image and a color characteristic image, the invention uses the black-and-white image Bm and the color image Cm to be a new black-and-white base image and a new color base image in next cycle and repeats the steps from step 304 and the follow-up image comparison until the last black-and-white image and the last color image are compared. For example, in the second cycle, the black-and-white image Bm (second black-and-white image), which is served as the black-and-white base image, is compared with the follow-up each black-and-white image B sequentially to determine the overlap index until the overlap index between the black-and-white image Bm and the follow-up another black-and-white image Bn (third black-and-white image) satisfies the black-and-white predetermined value (step 306). Then, the invention determines whether the overlap index between the color image Cm (second color image) and a color image Cn (third color image) corresponding to the black-and-white image Bn also satisfies the color predetermined value (step 308). If yes, it means that the black-and-white image Bn and the corresponding color image Cn can be set as the black-and-white characteristic image and the color characteristic image (step 310). Then, the invention uses the black-and-white image Bn (third black-and-white image) and the color image Cn (third color image) to be a new black-and-white base image and a new color base image to perform comparison for the third cycle until the last black-and-white image and the last color image are compared (step 304). Accordingly, the invention can determine a plurality of black-and-white characteristic images and a plurality of corresponding color characteristic images from the captured black-and-white images B and the captured color images C (step 204).

After the aforesaid method, the calculating unit 20 can determine a plurality of black-and-white characteristic images and a plurality of color characteristic images from the black-and-white images B and the corresponding color images C obtained by the ultrasound probe 10. Then, the calculating unit 20 can stitch the black-and-white characteristic images to form a black-and-white panoramic image and stitch the color characteristic images to form a color panoramic image. Then, the calculating unit 20 can overlay the color panoramic image with the black-and-white panoramic image to form a color Doppler panoramic image. Finally, the color output panoramic image can be displayed on the display unit.

The invention proposes a method for generating ultrasonic panoramic image and an ultrasonic device. The invention first analyzes the degree of overlap area between two black-and-white images and determines the Doppler signal error of two corresponding color images once the overlap area is large enough. A plurality of black-and-white characteristic images and color characteristic images are then determined from the captured black-and-white images and color images and used for generating a black-and-white panoramic image and a color panoramic image respectively using an image stitching algorithm. The color panoramic image is then overlaid with the black-and-white panoramic image to form an output panoramic image. Furthermore, a plurality of output panoramic images generated from different time points may further be outputted sequentially to form a continuous and dynamic panoramic image. Accordingly, the ultrasound panoramic scanning may obtain accurate and dynamic image result.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for generating ultrasonic panoramic image comprising steps of:

using an ultrasound probe to continuously obtain a plurality of black-and-white images and a plurality of color images from an object;

determining a plurality of black-and-white characteristic images from the plurality of black-and-white images and determining a plurality of color characteristic images from the plurality of color images, wherein the step of determining the plurality of black-and-white characteristic images from the plurality of black-and-white images and determining the plurality of color characteristic images from the plurality of color images comprises steps of:

setting a first black-and-white image to be a first black-and-white base image and a first black-and-white characteristic image and further setting a first color image to be a first color base image and a first color characteristic image;

after setting the first black-and-white image to be the first black-and-white base image and the first black-and-white characteristic image and further setting the first color image to be the first color base image and the first color characteristic image, determining whether an overlap index between the first black-and-white base image and a second black-and-white image in the plurality of black-and-white images satisfies a black-and-white predetermined value;

after determining the overlap index between the first black-and-white base image and the second black-and-white image satisfies the black-and-white predetermined value, determining whether an overlap index between the first color base image and a second color image in the plurality of color images satisfies a color predetermined value;

after determining the overlap index between the first color base image and the second color image satisfies the color predetermined value, setting the second black-and-white image to be a second black-and-white base image different from the first black-and-white base image and a second black-and-white characteristic image and further setting the second color image to be a second color base image different from the second color base image and a second color characteristic image; and after determining the overlap index between the first color base image and the second color image does not satisfy the color predetermined value, not setting the second black-and-white image to be the second black-and-white base image and the second black-and-white characteristic image and further not setting the second color image to be the second color base image and the second color characteristic image;

stitching the first black-and-white characteristic image and the second black-and-white characteristic image to form a black-and-white panoramic image and stitching the first color characteristic image and the second color characteristic image to form a color panoramic image; and overlaying the color panoramic image with the black-and-white panoramic image to form an output panoramic image.

2. The method of claim 1, wherein the overlap index between the first black-and-white base image and the second black-and-white image is generated according to a first characteristic algorithm.

3. The method of claim 1, wherein the overlap index between the first color base image and the second color image is generated according to a second characteristic algorithm.

4. The method of claim 1, wherein the step of determining the plurality of black-and-white characteristic images from the plurality of black-and-white images and determining the plurality of color characteristic images from the plurality of color images further comprises steps of:

after setting the second black-and-white image to be the second black-and-white base image and the second black-and-white characteristic image and further setting the second color image to be the second color base image and the second color characteristic image, determining whether an overlap index between the second black-and-white base image and a third black-and-white image in the plurality of black-and-white images satisfies the black-and-white predetermined value;

after determining the overlap index between the second black-and-white base image and the third black-and-white image satisfies the black-and-white predetermined value, determining whether an overlap index between the second color base image and a third color image in the plurality of color images satisfies the color predetermined value; and after determining the overlap index between the second color base image and the third color image satisfies the color predetermined value, setting the third black-and-white image to be a third black-and-white base image and a third black-and-white characteristic image and further setting the third color image to be a third color base image and a third color characteristic image.

5. The method of claim 1, wherein the step of stitching the first black-and-white characteristic image and the second black-and-white characteristic image to form the black-and-white panoramic image and stitching the first color characteristic image and the second color characteristic image to form the color panoramic image uses a stitching algorithm to stitch the first black-and-white characteristic image and the second black-and-white characteristic images to form the black-and-white panoramic image and stitch the first color characteristic image and the second color characteristic images to form the color panoramic image, and the stitching algorithm comprises one selected from a group consisting of Alpha mixed method, Poisson mixed method and multi-band mixed method.

6. The method of claim 1, further comprising steps of:

using the ultrasound probe to continuously obtain a plurality of first time series black-and-white images and a plurality of first time series color images from a first time point to generate a first output panoramic image; and using the ultrasound probe to continuously obtain a plurality of second time series black-and-white images and a plurality of second time series color images from a second time point to generate a second output panoramic image.

7. The method of claim 6, further comprising steps of:

displaying the first output panoramic image and the second output panoramic image to form a continuous and dynamic panoramic image.

8. An ultrasound device comprising:

an ultrasound probe continuously obtaining a plurality of black-and-white images and a plurality of color images from an object;

a processor determining a plurality of black-and-white characteristic images from the plurality of black-and-white images and determining a plurality of color characteristic images from the plurality of color images, the processor stitching the plurality of black-and-white characteristic images to form a black-and-white panoramic image and stitching the plurality of color characteristic images to form a color panoramic image, the processor overlaying the color panoramic image with the black-and-white panoramic image to form an output panoramic image; and a display unit displaying the output panoramic image;

wherein the plurality of black-and-white images comprises a first black-and-white image and a second black-and-white image, the plurality of color images comprises a first color image and a second color image, the plurality of black-and-white characteristic images comprises a first black-and-white characteristic image and a second black-and-white characteristic image, the plurality of color characteristic images comprises a first color characteristic image and a second color characteristic image, the processor sets the first black-and-white image to be a first black-and-white base image and the first black-and-white characteristic image and further sets the first color image to be a first color base image and the first color characteristic image; the processor determines whether an overlap index between the first black-and-white base image and the second black-and-white image satisfies a black-and-white predetermined value after setting the first black-and-white image to be the first black-and-white base image and the first black-and-white characteristic image and further setting the first color image to be the first color base image and the first color characteristic image; after determining the overlap index between the first black-and-white base image and the second black-and-white image satisfies the black-and-white predetermined value, the processor determines whether an overlap index between the first color base image and the second color image in the plurality of color images satisfies a color predetermined value; after determining the overlap index between the first color base image and the second color image satisfies the color predetermined value, the processor sets the second blackand-white image to be a second black-and-white base image different from the first black-and-white base image and the second black-and-white characteristic image and further sets the second color image to be a second color base image different from the first color base image and the second color characteristic image; and after determining the overlap index between the first color base image and the second color image does not satisfy the color predetermined value, the processor does not set the second black-and-white image to be the second black-and-white base image and the second black-and-white characteristic image and further not set the second color image to be the second color base image and the second color characteristic image.

9. The ultrasound device of claim 8, wherein the processor generates the overlap index between the first black-and-white base image and the second black-and-white image according to a first characteristic algorithm.

10. The ultrasound device of claim 8, wherein the processor generates the overlap index between the first color base image and the second color image according to a second characteristic algorithm.

11. The ultrasound device of claim 8, wherein the processor determines whether an overlap index between the second black-and-white base image and a third black-and-white image in the plurality of black-and-white images satisfies the black-and-white predetermined value after setting the second black-and-white image to be the second black-and-white base image and the second black-and-white characteristic image and further setting the second color image to be the second color base image and the second color characteristic image; after determining the overlap index between the second black-and-white base image and the third black-and-white image satisfies the black-and-white predetermined value, the processor determines whether an overlap index between the second color base image and a third color image in the plurality of color images satisfies the color predetermined value;

and after determining the overlap index between the second color base image and the third color image satisfies the color predetermined value, the processor sets the third black-and-white image to be a third black-and-white base image and a third black-and-white characteristic image and further sets the third color image to be a third color base image and a third color characteristic image.

12. The ultrasound device of claim 8, wherein the processor uses a stitching algorithm to stitch the plurality of black-and-white characteristic images to form the black-and-white panoramic image and stitch the plurality of color characteristic images to form the color panoramic image, and the stitching algorithm comprises one selected from a group consisting of Alpha mixed method, Poisson mixed method and multi-band mixed method.

13. The ultrasound device of claim 8, wherein the ultrasound probe continuously obtains a plurality of first time series black-and-white images and a plurality of first time series color images from a first time point and the processor generates a first output panoramic image accordingly; the ultrasound probe continuously obtains a plurality of second time series black-and-white images and a plurality of second time series color images from a second time point and the processor generates a second output panoramic image accordingly.

14. The ultrasound device of claim 13, wherein the display unit displays the first output panoramic image and the second output panoramic image to form a continuous and dynamic panoramic image.

\* \* \* \* \*